United States Patent
Lawrenson et al.

(10) Patent No.: US 11,412,321 B2
(45) Date of Patent: *Aug. 9, 2022

(54) METHOD AND APPARATUS FOR ADAPTIVE AUDIO SIGNAL ALTERATION

(71) Applicant: Telefonaktiebolaget LM Ericsson (publ), Stockholm (SE)

(72) Inventors: Matthew John Lawrenson, Bussigny (CH); Jan Jasper Van Den Berg, Lausanne (CH); Jacob Ström, Stockholm (SE); Lars Andersson, Solna (SE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/111,926

(22) Filed: Dec. 4, 2020

(65) Prior Publication Data

US 2021/0092508 A1 Mar. 25, 2021

Related U.S. Application Data

(63) Continuation of application No. 16/489,156, filed as application No. PCT/EP2017/056397 on Mar. 17, 2017, now Pat. No. 10,893,356.

(51) Int. Cl.
| | | |
|---|---|---|
| *H04R 1/10* | (2006.01) | |
| *A61B 5/38* | (2021.01) | |
| *G06F 3/16* | (2006.01) | |

(52) U.S. Cl.
CPC ............ *H04R 1/1083* (2013.01); *A61B 5/38* (2021.01); *G06F 3/165* (2013.01); *H04R 1/1041* (2013.01); *H04R 2460/01* (2013.01)

(58) Field of Classification Search
None
See application file for complete search history.

(56) References Cited

U.S. PATENT DOCUMENTS

| | | | | |
|---|---|---|---|---|
| 6,475,163 B1 * | 11/2002 | Smits | ................... | A61B 5/7203 |
| | | | | 600/559 |
| 2015/0297109 A1 * | 10/2015 | Garten | .................. | A61B 5/375 |
| | | | | 600/544 |

(Continued)

FOREIGN PATENT DOCUMENTS

| | | |
|---|---|---|
| EP | 2560412 A1 | 2/2013 |
| WO | 2016/175622 A1 | 11/2016 |

OTHER PUBLICATIONS

Anderson et al., "Translating Thoughts Into Actions by Finding Patterns in Brainwaves," Jan. 2008, Downloaded from the Internet: http://www.cs.colostate.edu/~anderson/wp/pubs/yale08.pdf on Aug. 23, 2019, 6 pages.

(Continued)

*Primary Examiner* — James K Mooney
(74) *Attorney, Agent, or Firm* — Nicholson De Vos Webster & Elliott LLP

(57) ABSTRACT

A method and an apparatus for enabling adaptive audio signal alteration are described. When an input audio signal is received, a determination of whether the user of an audio device hears the input audio signal is performed based upon brain activity of the user. A determination of whether the user is distracted by the audio signal is performed based upon sensor measurements indicating a physical state of the user. In response to determining that the user hears the input audio signal and that the input audio signal causes the user to be distracted, a determination of configuration parameter(s) is performed. An alteration of audio signal(s) is caused based upon the configuration parameter(s) to obtain modified version(s) of the audio signal(s) that are intended (Continued)

to address the distraction caused by the input audio signal, and output audio signals are output, where the output audio signals include the modified versions.

18 Claims, 10 Drawing Sheets

(56) References Cited

U.S. PATENT DOCUMENTS

| | | |
|---|---|---|
| 2016/0210407 A1 | 7/2016 | Hwang et al. |
| 2017/0041699 A1 | 2/2017 | Mackellar et al. |
| 2017/0061953 A1 | 3/2017 | An et al. |
| 2020/0029881 A1 | 1/2020 | Flood et al. |

OTHER PUBLICATIONS

California Ear Institute, "Auditory Steady State Response (ASSR)", retrieved from the Internet: http://www.Californiaearinstitute.com/audiology-services-assr-bay-area-ca.php, May 28, 2008, 1 page.
Cowan, Nelson, "Working Memory Underpins Cognitive Development, Learning, and Education", Educ Psychol Rev, Springer, retrieved from the Internet: http://link.springer.com/article/10.1007/s10648-013-9246-y, Decembers, 2013, 27 pages.
Doppler Labs Inc., "Here One—Wireless Smart Earbuds and a Connected App", retrieved from the Internet: https://hereplus.me/, Dec. 5, 2016, 5 pages.
Final Office Action, U.S. Appl. No. 16/489,156, dated Sep. 2, 2020, 11 pages.
Goverdovsky et al., "In-Ear EEG From Viscoelastic Generic Earpieces: Robust and Unobtrusive 24/7 Monitoring," IEEE Sensors Journal, Jan. 1, 2016, vol. 16, No. 1, pp. 271-277.
International Preliminary Reporton Patentability, PCT App. No. PCT/EP2017/056397, dated Sep. 26, 2019, 9 pages.
International Search Report and Written Opinion for Application No. PCT/EP2017/056397, dated Nov. 24, 2017, 10 pages.
Klingner et al., "Effects of visual and verbal presentation on cognitive load in vigilance, memory and arithmetic tasks", Stanford University, retrieved from the Internet: https://graphics.stanford.edu/papers/visual-cognitive-load/, Mar. 2011, 13 pages.
Metz, Rachel, "Using Your Ear to Track Your Heart", MIT Technology Review, retrieved from the Internet: https://www.technologyreview.com/s/529571/using-your-ear-to-track-your-heart/, Aug. 1, 2014, 4 pages.
Mikkelsen et al., "EEG Recorded from the Ear: Characterizing the Ear-EEG Method," Frontiers in Neuroscience, Nov. 18, 2015, vol. 9, Article. 438, Downloaded from the Internet: https://www.frontiersin.org/articles/10.3389/fnins.2015.00438/full on Aug. 23, 2019, 8 pages.
Non-Final Office Action, U.S. Appl. No. 16/489,156, dated Mar. 11, 2020, 11 pages.
Notice of Allowability, U.S. Appl. No. 16/489,156, dated Oct. 23, 2020, 11 pages.
Paulraj et al., "Auditory Evoked Potential Response and Hearing Loss: A Review," The Open Biomedical Engineering Journal, Feb. 2015, vol. 9, No. 1, Downloaded from the Internet: https://www.researchgate.net/publication/275217635_Auditory_Evoked_Potential_Response_and_Hearing_Lo . . . on Aug. 23, 2019, pp. 17-24 (9 pages).
U.S. Appl. No. 62/401,263 of 2020/0029881, filed Sep. 29, 2016, 20 pages.
Salai et al., "Stress Detection Using Low Cost Heart Rate Sensors", Hindawi Publishing Corporation, Journal of Healthcare Engineering, vol. 2016, Article ID 5136705, retrieved from the Internet: https://www.hindawi.com/journals/jhe/2016/5136705/, 2016, 13 pages.
Sauter et al., "ABR & ASSR: Challenges and Solutions, 2012", The Hearing Review, vol. 19, No. 6, retrieved from the Internet: https://www.hearingreview.com/miscellaneous/abr-amp-assr-challenges-and-solutions-2012, 2012, 11 pages.
Sorqvist et al., "How Concentration Shields Against Distraction", Association for Psychological Science, Current Directions in Psychological Science, vol. 24, No. 4, retrieved from the Internet: http://cdp.sagepub.com/contenl/24/4/267.full.pdf, 2015, pp. 267-272.
Strickland, Eliza, "In-Ear EEG Makes Unobtrusive Brain-Hacking Gadgets a Real Possibility", IEEE Spectrum, retrieved from the Internet: http://spectrum.ieee.org/the-human-os/biomedical/devices/in-ear-eeg-makes-unobtrusive-brain-hacking-gadgets-a-real-possibility, Jul. 7, 2016, 4 pages.
Thubron, Rob, "Amazon patents smart noise-canceling headphones that let you hear important external sounds", TechSpot, Inc., retrieved from the Internet: http://www.techspot.com/news/65791-amazon-patents-smart-noise-canceling-headphones-you-hear.html. Aug. 1, 2016, 2 pages.
Wikipedia, "Active noise control", retrieved from the Internet: https://en.wikipedia.org/wiki/Active_noise_control, Feb. 29, 2020, 3 pages.
Wikipedia, "Event-related potential", retrieved from the Internet: https://en.wikipedia.org/wiki/Event-related_potential, Feb. 29, 2020, 8 pages.
Zahran et al., "Evaluating Pupil Dilation as a Measure of Working Memory and Logical Thinking Manuscript", Grand Valley State University, ScholarWorks@GVSU, retrieved from the Internet: http://scholarworks.gvsu.edu/cgi/newcontent.cgi?article=1170&context=sss, Sep. 4, 2015, 11 pages.

\* cited by examiner

```
┌─────────────────────────────────────────────────────────────────────────┐
│  DETERMINE BASED UPON BRAIN ACTIVITY OF A USER OF THE AUDIO DEVICE,     │
│  WHETHER THE USER HEARS THE INPUT AUDIO SIGNAL                          │
│                              515                                         │
│                                                                          │
│        ┌──────────────────────────────────────────────────┐             │
│        │  RECEIVE ELECTROENCEPHALOGRAPHY (EEG) SENSOR     │             │
│        │  MEASUREMENTS LOCATED ON THE USER                │             │
│        │                     610                          │             │
│        └──────────────────────┬───────────────────────────┘             │
│                               ▼                                          │
│        ┌──────────────────────────────────────────────────┐             │
│        │  DETERMINE A CORRELATION BETWEEN THE EEG SENSOR  │             │
│        │  MEASUREMENTS AND THE INPUT AUDIO SIGNAL         │             │
│        │                     615                          │             │
│        └──────────────────────┬───────────────────────────┘             │
│                               ▼                                          │
│        ┌──────────────────────────────────────────────────┐             │
│        │  COMPARE THE CORRELATION BETWEEN THE EEG SENSOR  │             │
│        │  MEASUREMENTS AND THE INPUT AUDIO SIGNAL WITH    │             │
│        │  ONE OR MORE AUDITORY EVOKED POTENTIAL (AEP)     │             │
│        │  SIGNATURES TO DETERMINE WHETHER THE USER HEARS  │             │
│        │  THE INPUT AUDIO SIGNAL AND TO IDENTIFY ONE OR   │             │
│        │  MORE AEP EVENTS ASSOCIATED WITH THE INPUT AUDIO │             │
│        │  SIGNAL, WHERE EACH OF THE AEP SIGNATURES IS     │             │
│        │  REPRESENTATIVE OF EEG SENSOR MEASUREMENTS       │             │
│        │  ASSOCIATED WITH AUDIO SIGNALS                   │             │
│        │                     620                          │             │
│        └──────────────────────────────────────────────────┘             │
└─────────────────────────────────────────────────────────────────────────┘
```

Figure 6

```
┌─────────────────────────────────────────────────────────────────────────┐
│  DETERMINE BASED UPON SENSOR MEASUREMENTS INDICATING A PHYSICAL STATE   │
│  OF THE USER, THAT THE USER IS DISTRACTED BY THE INPUT AUDIO SIGNAL     │
│                              520                                         │
└─────────────────────────────────────────────────────────────────────────┘

┌─────────────────────────────────────────────────────────┐
        │  DETERMINE THAT AT LEAST ONE OF THE SENSOR MEASUREMENTS │
        │  INDICATING A PHYSICAL STATE OF THE USER, IS ABOVE A    │
        │  DISTRACTION THRESHOLD                                   │
        │                      710                                 │
        └─────────────────────────────────────────────────────────┘
                                    │
                                    ▼
        ┌─────────────────────────────────────────────────────────┐
        │  DETERMINE A CORRELATION BETWEEN THE AT LEAST ONE       │
        │  SENSOR MEASUREMENT AND THE INPUT AUDIO SIGNAL          │
        │                      715                                 │
        └─────────────────────────────────────────────────────────┘
```

Figure 7

METHOD AND APPARATUS FOR ADAPTIVE AUDIO SIGNAL ALTERATION

CROSS-REFERENCE TO RELATED APPLICATIONS

This application is a continuation of application Ser. No. 16/489,156, filed Aug. 27, 2019, which is a National stage of International Application No. PCT/EP2017/056397, filed Mar. 17, 2017, which are hereby incorporated by reference.

TECHNICAL FIELD

The invention relates to a method of enabling adaptive audio signal alteration, an apparatus for enabling adaptive audio signal alteration, and a machine-readable medium comprising computer program code.

BACKGROUND ART

Augmented Hearing or Active/Smart Noise Cancellation is a technology embodied in headphones or earbuds that enables user to selectively block or alter sounds present in the user's environment. Existing techniques enabling augmented hearing shield the user from their surrounding sounds, record these sounds, alter some or all of these sounds, and play them back to the user. For example, this process can be performed by applying a filter to the sounds and optionally using noise-cancellation techniques for suppressing the sounds entirely. These techniques can typically be performed in real-time (with unperceivable latency) and blocking or filtering of the sounds can be done on the full incoming soundwaves or on parts of the soundwaves forming the sounds (e.g., certain frequency ranges can be altered or blocked).

Some existing augmented hearing techniques are based on noise volume. For example, in a first approach, a microphone is used to capture an ambient sound, and an audio wave that is in antiphase with the captured sound is generated resulting in the cancellation of the captured ambient sound. The amplitude of the generated anti-sound can be varied, based on the captured ambient sound. In another approach, the ambient sound is first blocked and then replayed at a lower volume. The volume of the replayed sound can be varied based on the captured ambient sound. In other approaches, filters can be used for selecting ambient sounds that are to be altered or blocked. For instance, high or low pass filters can be used for selectively blocking or lowering the volume of ambient sounds with frequencies within a given unwanted frequency range.

Some existing augmented hearing techniques are based on noise classification. In these solutions, digital signal processing mechanisms enable an increased control over the augmented sound. For example, an audio sample of ambient sound can be analysed to extract various sounds, which are classified into different sounds. Following the classification, different attenuation levels and/or filters can be applied to different classes (which can be specified according to the user's preferences).

However, the existing solutions of augmented hearing have several drawbacks and disadvantages. In all existing solutions providing augmented hearing to a user of an audio device, the operations performed by the audio device are in response to a predetermined set of conditions (e.g., blocking/altering sounds of a given volume, or of a particular class of sounds). However, these techniques do not take into consideration the effect that certain sounds have over the user may change over time. Further, in these solutions, if the user adapts these settings manually to respond to true distractions rather than responding to certain characteristics of the incoming sound, the solution is reactive instead of proactive.

In addition, none of the existing solutions can determine if the user has heard a certain incoming sound or if the augmented sound that reaches the ear is in fact heard by the user. This can result in unwanted situations, where the altered sound is either blocked entirely resulting in an eerie silence or is still too loud for the user even after attenuation. Similarly, selectively blocking or modifying certain sounds or certain classes of sounds (e.g. a certain person's speech or certain type of noise), leads to a somewhat unnatural feeling experienced by the user. For example, clipping certain frequencies could make desired noises sound strange, while a lack of correlation between audio and what is happening around the user can lead to unwanted consequences (people that are talking to the user are not being heard, people are appearing next to the user when the user was not aware of their presence, etc.).

SUMMARY OF THE INVENTION

It is an object of the invention to provide an improved alternative to the above techniques and prior art.

One general aspect includes a method of enabling adaptive audio signal alteration, the method including: receiving an input audio signal; determining, based upon brain activity of a user of an audio device, whether the user hears the input audio signal; determining, based upon sensor measurements indicating a physical state of the user, whether the user is distracted by the input audio signal; and, in response to determining that the user hears the input audio signal and that the input audio signal causes the user to be distracted, determining one or more configuration parameters to be used for altering one or more audio signals; causing an alteration of the one or more audio signals based upon the one or more configuration parameters to obtain one or more modified versions of the one or more audio signals that are intended to address the distraction caused by the input audio signal; and causing one or more output audio signals to be output, where the one or more output audio signals include the modified versions of the one or more audio signals.

Embodiments of the invention may include one or more of the following features. The method where the determining whether a user of the audio device hears the input audio signal includes: receiving electroencephalography (EEG) sensor measurements from an EEG sensor located on the user; determining a correlation between the EEG sensor measurements and the input audio signal; and comparing the correlation between the EEG sensor measurements and the input audio signal with one or more auditory evoked potential AEP signatures to determine whether the user hears the input audio signal and to identify one or more AEP events associated with the input audio signal, where each of the AEP signatures is representative of EEG sensor measurements associated with audio signals.

In some embodiments, determining one or more configuration parameters to be used for altering one or more audio signals includes setting an acoustic level of the input audio signal to be a distraction acoustic level threshold.

In some embodiments, causing an alteration of the one or more audio signals includes causing the input audio signal to be blocked from being output to the user based upon the distraction acoustic level threshold.

In some embodiments, determining one or more configuration parameters to be used for altering one or more audio signals includes determining an acoustic level decrease parameter.

In some embodiments, causing an alteration of the one or more audio signals includes causing an acoustic level of the input audio signal to be decreased based upon the acoustic level decrease parameter and the distraction acoustic level threshold, prior to being output to the user.

In some embodiments, determining one or more configuration parameters to be used for altering one or more audio signals includes determining an acoustic level increase parameter.

In some embodiments, causing an alteration of the one or more audio signals includes causing an acoustic level of a second audio signal to be increased based upon the acoustic level increase parameter and the distraction acoustic level threshold, prior to being output to the user.

In some embodiments, the sensor measurements include at least one of electroencephalography (EEG) sensor measurements, motion sensor measurements, heart rate sensor measurements, breathing sensor measurements, and productivity monitoring measurements.

In some embodiments, determining whether the user is distracted by the input audio signal includes determining that at least one of the sensor measurements indicates a physical state of the user is above a distraction threshold.

In some embodiments, determining whether the user is distracted by the input audio signal includes determining a correlation between the at least one sensor measurement and the input audio signal.

One general aspect includes an apparatus for enabling adaptive audio signal alteration, the apparatus including: an audio signal adaptive alteration unit operative to perform the operations of receiving an input audio signal; determining, based upon brain activity of a user of the apparatus, whether the user hears the input audio signal; and determining, based upon sensor measurements indicating a physical state of the user, whether the user is distracted by the input audio signal. The audio signal adaptive alteration unit is further operative to, in response to determining that the user hears the input audio signal and that the input audio signal causes the user to be distracted, determine one or more configuration parameters to be used for altering one or more audio signals, cause an alteration of the one or more audio signals based upon the one or more configuration parameters to obtain one or more modified versions of the one or more audio signals that are intended to address the distraction caused by the input audio signal, and cause one or more output audio signals to be output, where the one or more output audio signals include the modified versions of the one or more audio signals

BRIEF DESCRIPTION OF THE DRAWINGS

The invention may best be understood by referring to the following description and accompanying drawings that are used to illustrate embodiments of the invention. In the drawings:

FIG. 6 illustrates a flow diagram of exemplary operations for determining, based upon brain activity of a user, whether a user of an audio device hears an audio signal, in accordance with some embodiments.

FIG. 7 illustrates a flow diagram of exemplary operations for determining, based upon sensor measurements indicating a physical state of the user, whether the user is distracted by an audio signal, in accordance with some embodiments.

DETAILED DESCRIPTION

Figure 1:
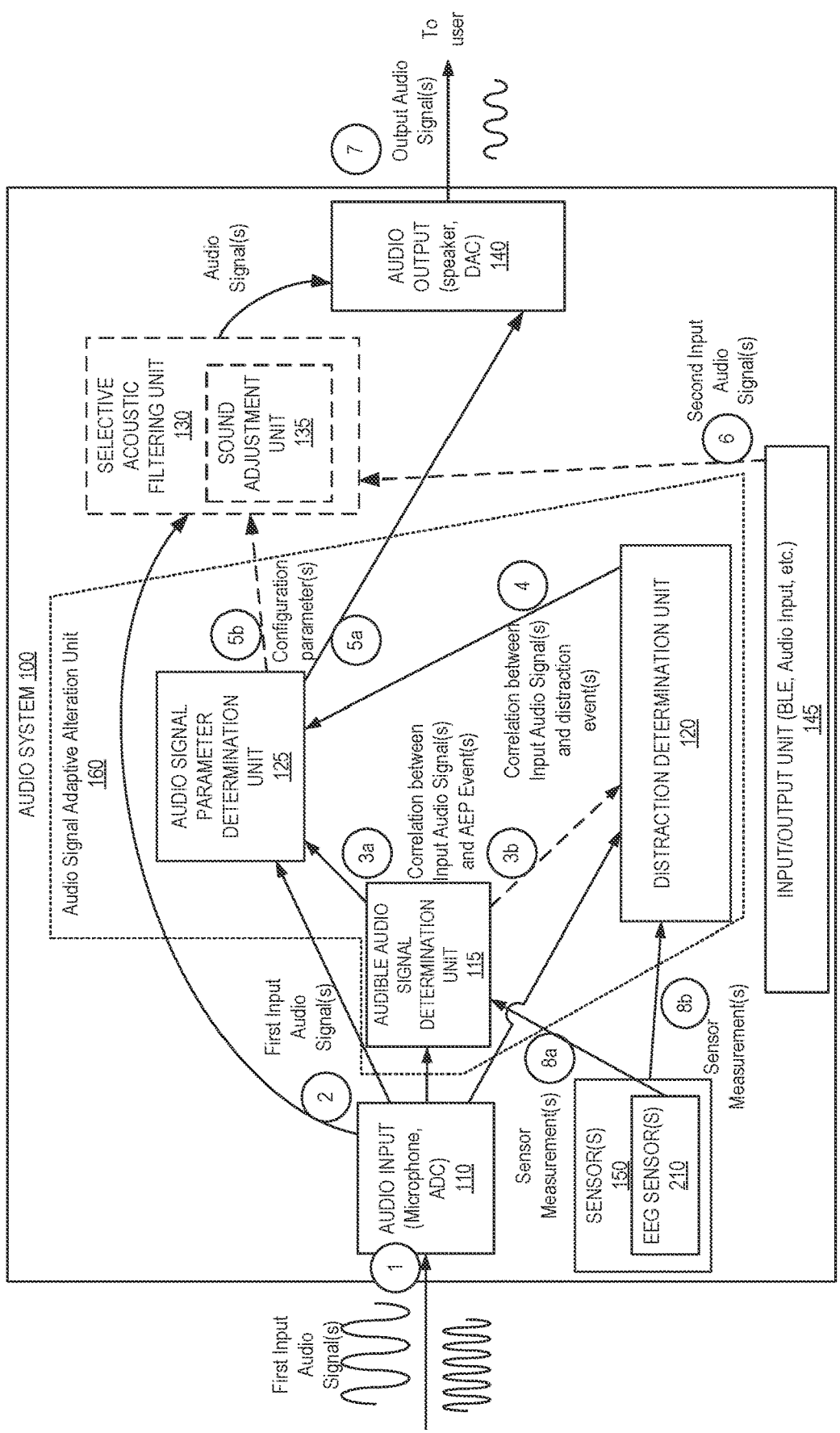
FIG. 1 illustrates a block diagram of an exemplary audio system 100 for enabling adaptive audio signal alteration, in accordance with some embodiments.

The following description describes methods and apparatus for adaptive audio signal alteration. In the following description, numerous specific details such as logic implementations, opcodes, means to specify operands, resource partitioning/sharing/duplication implementations, types and interrelationships of system components, and logic partitioning/integration choices are set forth in order to provide a more thorough understanding of the present invention. It will be appreciated, however, by one skilled in the art that the invention may be practiced without such specific details. In other instances, control structures, gate level circuits and full software instruction sequences have not been shown in detail in order not to obscure the invention. Those of ordinary skill in the art, with the included descriptions, will be able to implement appropriate functionality without undue experimentation.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Bracketed text and blocks with dashed borders (e.g., large dashes, small dashes, dot-dash, and dots) may be used herein to illustrate optional operations that add additional features to embodiments of the invention. However, such notation should not be taken to mean that these are the only options or optional operations, and/or that blocks with solid borders are not optional in certain embodiments of the invention.

In the following description and claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other.

Electroencephalography (EEG) is a non-invasive technology for monitoring brain activity across different mental states using electrodes that probe time-varying electric fields created by the firing of neurons. Some EEG systems use electrodes placed on the scalp of a subject. Recent scientific and technological developments make use of two-channel EEG monitoring system using in-ear devices (e.g., K. B. Mikkelsen, S. L. Kappel, D. P. Mandic, P. Kidmose, "EEG Recorded from the Ear: Characterizing the Ear-EEG Method", in Frontiers in Neuroscience, vol. 9, article 438, 2015; and V. Goverdovsky, D. Looney, P. Kidmose, and D. P. Mandic, "In-Ear EEG From Viscoelastic Generic Earpieces: Robust and Unobtrusive 24/7 Monitoring," in IEEE Sensors Journal, vol. 16, pages 271-277, 2016.).

In-ear EEG devices have similar performance as conventional EEG for several responses paradigms, i.e., signals caused as a response to external stimuli called Event-Related Potentials (ERPs). In-ear EEG has been shown to be as effective as on-scalp EEG for spectrogram-based analysis, has similar timing of ERP components and has an equal signal strength for sources close to the ear.

Auditory Evoked Potentials (AEPs) measurements are a sub-category of ERPs that can be detected in the subject's EEG measurements after an auditory stimulus. As described in "Auditory Evoked Potential Response and Hearing Loss: A Review" (by M. P. Paulraj, K. Subramaniam, S. Bin Yaccob, A. H. Bin Adom, and C. R. Hema, The Open Biomedical Engineering Journal, vol. 9, pages 17-24, 2015), AEP measurements can be used for the automatic detection of hearing loss, especially for babies or patients that are unable to properly communicate during a hearing test. An example of an AEP is the Auditory Steady-State Response (ASSR), which is the EEG response to amplitude modulated stationary white noise, where the neural response is detected to fluctuate with the frequency of the amplitude modulation. The ASSR can be detected using in-ear EEG. EEG signals related to AEPs are generally orders of magnitude lower than several forms of background noise, e.g. from non-relevant brain activity, noise caused by muscle nerve activation (myogenic noise) and electromagnetic background.

Concentration makes people less susceptible to distraction, but involves considerable cognitive straining. The extent to which people can focus on a certain task depends on the exact nature and difficulty of that task and the modality (e.g., visual, verbal) of the distraction in comparison with the task. Competing sensory inputs (distractions) can result in high working memory load, which can limit one's cognitive capabilities.

Latest developments have shown that EEG measurements can be linked to cognitive tasks. For example, Anderson and Bratman showed (in "Translating Thoughts into Actions by Finding Patterns in Brainwaves," Department of Computer Science, Colorado State University, 2008) that EEG measurements can be used to classify a mental task from five options with an accuracy of 80%. Other mechanisms used to measure if a person is distracted might be by detecting any unwanted negative emotions (and possibly their correlation to distracting inputs), such as stress or annoyance. These can be measured by monitoring vital signs (e.g., using in-ear heart rate monitors) of a person.

The embodiments described below provide a method and an apparatus for enabling adaptive audio signal alteration. The embodiments enable the adaptive alteration of sounds to which a user is exposed based upon a determination of whether the user hears the sounds and on whether the user is distracted by these sounds. In particular, when an input audio signal is received, a determination of whether the user of an audio device hears an audio signal is performed based upon brain activity of the user. A determination of whether the user is distracted by the input audio signal is performed based upon sensor measurements indicating a physical state of the user. In response to determining that the user hears the input audio signal and that the input audio signal causes the user to be distracted, a determination of one or more configuration parameters to be used for altering one or more audio signals is performed. An alteration of the one or more audio signals is caused based upon the one or more configuration parameters to obtain one or more modified versions of the one or more audio signals that are intended to address the distraction caused by the input audio signal, and one or more output audio signals are caused to be output, where the one or more output audio signals include the modified versions of the one or more audio signals.

FIG. 1 illustrates a block diagram of an exemplary audio system 100 for enabling adaptive audio signal alteration, in accordance with some embodiments. The audio system 100 includes an audio input 110, an audio signal adaptive alteration unit (AAU) 160, an audio output 140, an Input/Output unit 145, one or more sensor(s) 150 that includes EEG sensor(s) 210, and optionally a selective acoustic filtering unit (SAFU) 130 that may include a sound adjustment unit (SAU) 135. The AAU 160 includes an audible audio signal determination unit (ADU) 115, and a distraction determination unit (DDU) 120. In some embodiments, as will be described in further detail with reference to FIGS. 9, 10A-B, the audio system 100 may be implemented as a single audio device being worn by a user (e.g., headphones, earbuds, etc.). In other embodiments, the audio system 100 may be implemented as two or more devices, where each device may include some but not all of the components of the audio system 100.

The audio system 100 is operative to receive input audio signal(s) (e.g., first and second input audio signals) and analyze the signal(s) in correlation with EEG sensor measurements and distraction events to adapt and alter the audio signal(s) to be output to the user of an audio device with the intention to address the distraction caused by the audio signal(s) (e.g., by causing a reduction of a distraction to the user of the audio device or ending the distraction). With reference to FIG. 1, at operation 1, first input audio signal(s) are received at the audio input 110. In some embodiments, the audio input includes a microphone operative to convert incoming sounds into electrical input audio signal(s). In some embodiments, the audio device may include an Analog-to-Digital (ADC) converter operative to convert input audio signal(s) into a digital input audio signal(s). In alternative embodiments, the microphone is included in a device that is separate from the audio system 100, and the audio signal(s) are received at the audio input 110 in a digitized format. The operations described below with reference to the other components of the audio system are operative to analyze and alter an analog input audio signal or a digital audio signal without departing from the scope of the present invention.

The first input audio signal(s) may include one or more soundwaves (representing different sounds) that can be distinguishable one over the other. Each one of the first input audio signal(s) is associated with a time interval indicating the time at which the signal is received at the audio system 100. The first input audio signal(s) correspond to ambient sounds from the environment of the user of an audio device. For example, the user may be located in a work place, where conversations of colleagues, various background noises, street noises, etc. can be heard. Various examples of surrounding environment can be contemplated. As described above or in further details below, the audio device is typically worn by the user and can include all or a portions of the components of the audio system 100. In the following description a user of the audio device will refer to a user of the audio system 100 when the audio system is included in a single audio device, or alternatively to a user of an audio device that includes only a subset of the components of the audio system 100.

The audio system 100 may further receive other input audio signals (second input audio signal) from an audio input at operation 6. These second audio signals can be received from a media player (e.g., music player, video player, etc.) that the user is using to listen to controlled or selected sounds (e.g., music, podcasts, radio program, etc.). Thus, as opposed to the first input audio signals on which the user has little control, the user has greater control on these second input audio signals as they can select the content and the volume of these signals.

Once the first input audio signal(s) are received at the audio input 110, they are transmitted, at operation 2, to the ADU 115, to the DDU 120, and to the PDU 125. In some embodiments, the first input audio signal(s) can be transmitted to the SAFU 130. In some embodiments, the SAFU 130 can be a piece of material that fully or partially absorbs the first input audio signal(s). For example, a material can be used that can mechanically change its properties to selectively absorb certain frequencies or features of the first input audio signal(s). In other embodiments, the first input audio signal(s) are directly transmitted to the audio output, which includes speaker(s) (and optionally a digital to analog (DAC) converter) to be output to the user as output audio signal(s).

The ADU 115 is operative to determine whether the user of the audio device hears the input audio signal(s), based upon brain activity of a user of the audio device. The ADU 115 is communicatively coupled with the sensor(s) 150, the PDU 125, the audio input 110, and optionally with the DDU 120. The ADU 115 receives the first audio input signal(s) from the audio input 110 and receives sensor measurements from the sensor(s) 150. In particular, the ADU 115 receives EEG sensor measurements (8a) from the EEG sensor(s) 210 and determines a correlation between the first input audio signal(s) and AEP events associated with the EEG sensor measurements. The correlation between the first input audio signal(s) and the AEP events is transmitted to the PDU 125 and optionally to the DDU 120. The correlation between the first input audio signal(s) and the AEP events provides an indication of whether the input audio signal(s) are heard by the user of the audio device. In some embodiments, when several first input audio signals are received at the ADU 115, the ADU 115 may determine that only a subset of these signals (e.g., a single signal or N signals, etc.) are heard by the user. In some of these embodiments, the ADU 115 outputs a correlation and correspondence between AEP events and each one of the input audio signals that are heard, while discarding the audio signals that did not trigger AEP events (i.e., that are not heard by the user).

Figure 2:
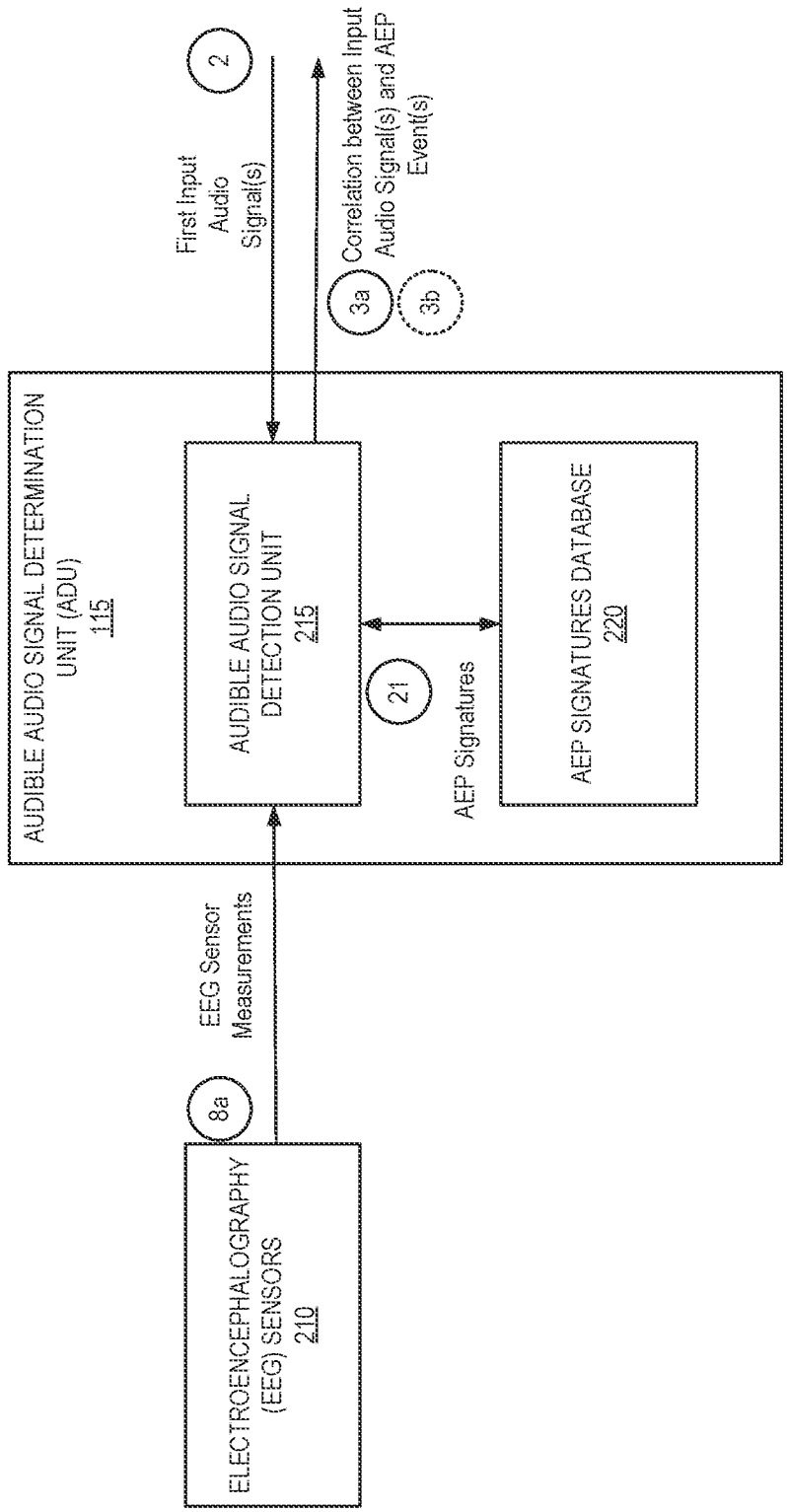
FIG. 2 illustrates a block diagram of an exemplary audible audio signal determination unit for determining, based upon brain activity of a user, whether a user of an audio device hears an audio signal, in accordance with some embodiments.

In some embodiments, the ADU 115 is operative to perform the operations as described in further detail with reference to FIG. 2. FIG. 2 illustrates a block diagram of an exemplary audible audio signal determination unit 115 for determining, based upon brain activity of a user, whether a user of an audio device hears an audio signal, in accordance with some embodiments. The ADU 115 includes an audible audio signal detection unit 215 coupled with an AEP signatures database 220. The audible audio signal detection unit 215 is coupled with EEG sensors 210. While in the illustrated embodiment of FIG. 2, the EEG sensors are external to the ADU 115, in other embodiments, the EEG sensors 210 can be included in the ADU 115 and communicatively coupled with the audible audio signal detection unit 215.

The audible audio signal detection unit 215 receives the first input audio signal(s) (at operation 2) and the EEG sensor measurements (operation 8a). Each one of the first audio signal(s) is associated with respective times indicating the time at which the signal was received at the audio system 100. In some embodiments, the audible audio signal detection unit 215 is operative to pre-process the raw EEG sensor measurements, e.g., by amplifying parts of the signal that are of interest, and/or by removing noise. As described above, the EEG sensor measurements are representative of the EEG brain activity of the user of the audio device. In some embodiments, the EEG sensors includes in-ear EEG sensors and the EEG sensor measurements are in-ear sensor measurements. In other embodiments, other types of EEG sensors may be used (e.g., on scalp EEG sensors or around-ear EEG sensors) without departing from the scope of the present invention.

The AEP signatures database 220 includes values or characteristics of typical EEG sensor measurements (i.e., the "AEP Signatures") that can be detected when a sound is heard by the user, i.e., when a sound (i.e., input audio signal) causes a detectable AEP (the "AEP Event") such as a peak in the EEG measurements being detected within a given time delay (within a given time interval) after the sound reaches the user's ear. In some embodiments, the AEP signatures may be obtained during a learning phase during which EEG measurements of a user are acquired and analyzed in correlation with predetermined sounds being output to the user. For example, in some embodiments, during this learning phase the user may be submitted to various sound types and various sound volumes at regular intervals during a predetermined period of time, while EEG measurements are recorded and AEP events detected in correlation with the sounds. In some embodiments, the AEP signatures are generated for a particular user (the one using the audio device), while in other embodiments the AEP signatures may be generated for several users (including or not the current user of the audio device).

The audible audio signal detection unit 215 is operative to perform an AEP Reading (i.e., determining one or more AEP events associated with each one of the first input audio signals) based upon the received EEG sensor measurements 8a, the first input audio signal(s) 2, and the AEP signatures 21 from the AEP signatures database 220. The audible audio signal detection unit 215 determines whether the user of the audio device hears each one of the first input audio signals by detecting AEP events that are associated (i.e., that correlates) with that first input audio signal. For example, for a given first input audio signal, the audible audio signal detection unit 215 can determine that within a given interval of time from the time that first input audio signal was received at the audio input (or alternatively from the time the first input audio signal is output at the audio output to the user without being modified), an EEG sensor measurement that corresponds to an AEP event is detected and therefore providing an indication that the user hears the input audio signal. In another example, an audio signal output to the user may not have been heard and EEG sensor measurements obtained would not lead to the detection of an AEP event corresponding to a sound heard. Therefore, the audible audio signal detection unit 215 determines whether or not the user hears each one of the first input audio signals and outputs (3a, 3b) a correlation determined between the input audio signals and AEP events that is indicative of whether the user hears the audio signal(s) or not.

In some embodiments, the first input audio signal(s) from the environment of the user may include several distinct sounds. While these sounds may all input the audio device (e.g., they may be recorded by a microphone of the audio input), not all the sounds can be heard by the user of the audio device user. Therefore, in these embodiments, the ADU 115, and in particular the audible audio signal detection unit 215 are operative to identify the sounds (and corresponding input audio signal(s)) that are actually being heard by the user and distinguishing them from the set of sounds input to the audio system 100.

Referring back to FIG. 1, the DDU 120 is operative to determine whether the user is distracted by the input audio signal(s) based upon sensor measurements indicating a physical state of the user. The DDU 120 is communicatively coupled with the sensor(s) 150, the PDU 125, the audio input 110, and optionally with the ADU 115. The DDU 120 receives the first audio input signal(s) from the audio input 110 and receives sensor measurements (8b) from the sensor(s) 150, and determines a correlation between the input audio signal(s) and distractions events associated with the sensor measurements. The correlation between the input audio signal(s) and distractions events is transmitted (operation 4) to the PDU 125 and provides an indication of whether the input audio signal(s) cause a distraction of the user.

Figure 3:
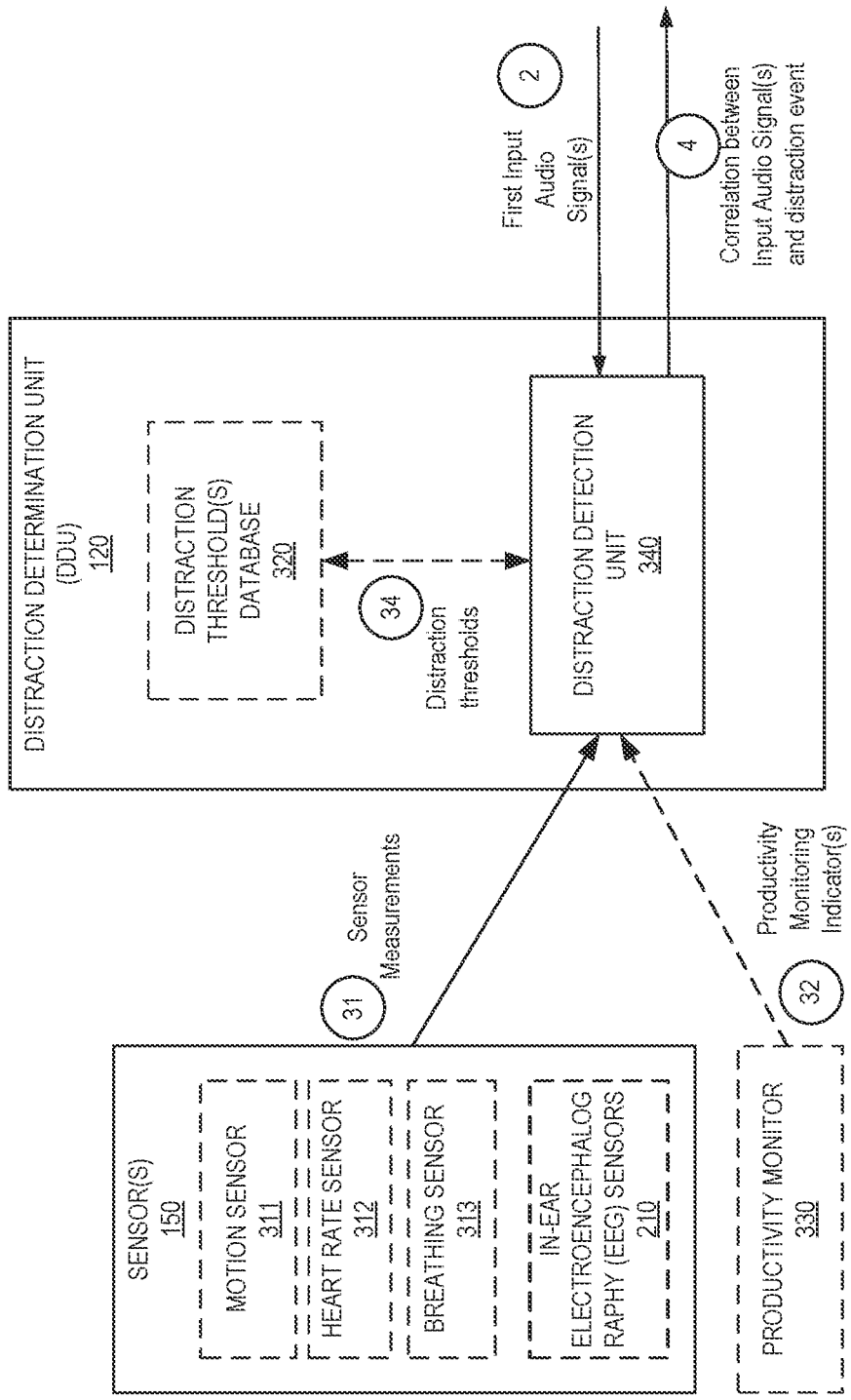
FIG. 3 illustrates a block diagram of an exemplary distraction determination unit for determining, based upon sensor measurements indicating a physical state of the user, whether the user is distracted by an audio signal, in accordance with some embodiments.

In some embodiments, the DDU 120 is operative to perform the operations as described in further detail with reference to FIG. 3. FIG. 3 illustrates a block diagram of an exemplary distraction determination unit 120 for determining, based upon sensor measurements indicating a physical state of the user, whether the user is distracted by an audio signal, in accordance with some embodiments. The DDU 120 includes a distraction detection unit 340 that is coupled with the sensor(s) 310. The DDU 120 may optionally include a distraction thresholds database 320, and may be optionally coupled with the productivity monitor 330. The sensor(s) 150 may include one or more sensors that are operative to determine a physical state of the user that can provide an indication of whether or not the user is distracted by a given input audio signal (i.e., by a given sound).

In some embodiments, the sensor(s) 150 can include one or several of the following sensors: a motion sensor 311, a heart rate sensor 312, a breathing sensor 313, and EEG sensors 210. The motion sensor 311 is operative to determine movement of the user. In particular, the sensor measurements obtained from the motion sensor are used to detect certain movements of the user that are indicative of the user being distracted by the sounds they hear, e.g., the user turns their head towards the sound. The heart rate sensor 312 is operative to measure the heart rate of the user. The breathing sensor 313 is operative to measure the user's breathing patterns. The regularity of the vital signs of the user (e.g., heart rate measurements, breathing patterns, etc.) can be influenced by distractions to the user, e.g., the user's focus, the user's mental load, the user's negative emotions that might be caused by distracting sounds. The EEG sensors 210 are operative to measure certain signatures (other than the AEP Signatures) that are indicative of the user being distracted, e.g., the user's mood, level of relaxation, etc. In some embodiments, the sensor(s) 150 may include all of the illustrated sensor(s), while in other embodiments, the sensor(s) may include only a subset of the illustrated set (where the subset is strictly less than the entire set). While in the illustrated embodiment of FIG. 3, the sensor(s) 150 are external to the DDU 120, in other embodiments, the sensor(s) 150 can be included in the DDU 120 and communicatively coupled with the distraction detection unit 340.

The distraction detection unit 340 is coupled with the productivity monitor 330 that is operative to detect the user being distracted, by measuring the behavior of the user while performing a task (e.g., using a smartphone, a computer, fitness and exercise equipment, etc.), e.g., by measuring the user's efficiency. The productivity monitor 330 is operative to monitor the task performed by the user and detect that the user is being distracted from performing the task at a regular or efficient rate. The productivity monitor 330 is operative to communicate productivity monitoring indicator(s) 32 to the distraction detection unit 340. In some embodiments, the productivity monitor 330 is an external element that is located within another device being used by the user of the audio device (e.g., smartphone, computer, exercise and fitness equipment, etc.) for performing an activity. In these embodiments, the DDU 120 may receive the productivity monitoring indicator(s) through the input/output unit 145 of the audio system 100 (e.g., through a Bluetooth Low Energy (BLE) interface).

The distraction detection unit 340 receives the sensor measurements and the input audio signal(s) and determines whether the input audio signal(s) cause a distraction of the user. In some embodiments, the distraction detection unit 340 determines that at least one of the sensor measurements received is above a distraction threshold associated with the sensor measurement indicating that the user is being distracted at the moment in time associated with the sensor measurements analyzed. The distraction detection unit 340 further determines if there is a correlation, at that given moment in time, between the sensor measurement (that is above the distraction threshold) and at least one of the input audio signal(s). In one embodiment, the distraction threshold can be a single value used to determine whether sensor measurements are indicative of a state of a user being distracted. In other embodiments, the DDU 120 includes a distraction threshold database 320 which includes a set of distraction thresholds to be used for determining whether the user is distracted or not. For example, this can be used in the embodiments where there are several sensor(s) 150 and each type of sensors can be associated with a respective distraction threshold stored in the database 320. In other embodiments, instead of being associated with respective sensors, each one of the distraction thresholds can be associated with a respective input audio signal (i.e., with a respective sound) that can be received at the audio input, such that each input audio signal is associated with a respective distraction threshold. In other embodiments, the different distraction thresholds can also be associated with various tasks or activities being performed by the user, such that indicators received from the productivity monitor 330 can be indicative of several activities and each one is associated with a respective distraction threshold from the database 320.

The distraction detection unit 340 outputs a correlation (4) between the input audio signals and the distraction events detected. The distraction events are representative of the user being distracted at a given moment in time and result from the analysis of the sensor measurements and the productivity monitoring indicators with respect to the distraction thresholds.

Referring back to FIG. 1, based upon the correlation between the input audio signal(s), the AEP event(s) and the distraction event(s), the PDU 125 is operative to determine that the user hears an input audio signal from the input audio signals and that the input audio signal causes the user to be distracted. In response to determining that the user hears the input audio signal and that the input audio signal causes the user to be distracted, the PDU 125, determines one or more configuration parameters (5a and optionally 5b) to be used for altering one or several ones of the input audio signals prior to them being output at the audio output 140. In other words, the PDU 125 upon determining that the user is distracted by one or more sounds (represented by the first input audio signal(s)), it determines to what extent this or these sounds should be altered to create a non-distractive audio signal that is more natural than a complete sound blocking/cancellation. The configuration parameters (5a) are used to configure the audio output 140 for processing the input audio signal(s) that are to be output to the user. In some embodiments, the configuration parameters can be transmitted to the sound adjustment unit 135 to be used for processing the input audio signal(s) prior to them being output to the user (through the audio output 140).

The PDU 125 further causes an alteration of the audio signals based upon the configuration parameters to obtain modified versions of the audio signals that are intended to address the distraction caused by the audio signal. The PDU 125 further causes (operation 7) the output of output audio signals. The output audio signals include the modified versions of the audio signals such that these modified versions of the audio signals address the distraction caused by the audio signal to the user.

Figure 4:
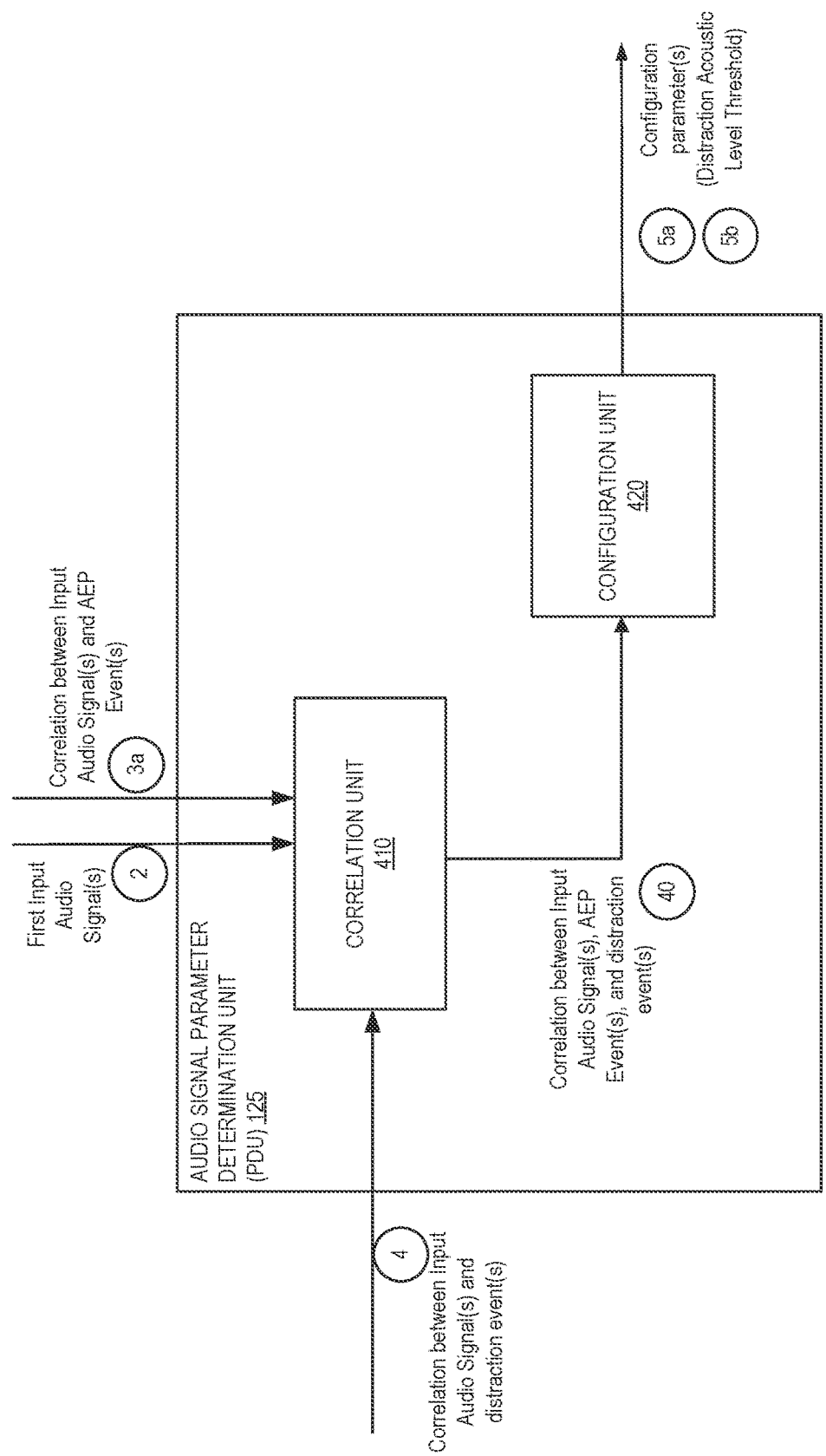
FIG. 4 illustrates a block diagram of an exemplary audio signal parameter determination unit, in accordance with some embodiments.

In some embodiments, the PDU 125 is operative to perform the operations as described in further detail with reference to FIG. 4. FIG. 4 illustrates a block diagram of an exemplary audio signal parameter determination unit, in accordance with some embodiments. The PDU 125 includes a correlation unit 410 and a configuration unit 420. While the audio system 100 may receive one or multiple audio signals, the operations below of the PDU 125 will be described with reference to a single input audio signal for ease of understanding. However, a person of ordinary skill in the art would understand that the elements of the PDU 125 are not so limited and may perform operations on more than one input audio signal. The correlation unit receives a first input audio signal (2); the correlation between the input audio signal and the AEP events (3a) indicating whether or not the input audio signal is heard; and a correlation between the input audio signal and the distraction events (4) indicating whether or not the input audio signal is causing a distraction of the user. The correlation unit 410 analyzes the several inputs and determines a correlation between the input audio signal, the AEP events, and the distraction events consequently determining if an input audio signal (and which input audio signal if several are received) is heard by the user and causes a distraction of the user at a given moment in time. The correlation between the input audio signal, the AEP events and the distraction events is transmitted to the configuration unit 420. For example, this correlation may include an identification of an input audio signal from the input audio signal(s) causing the distraction and an indication that it is in fact causing the distraction.

The configuration unit 420, upon receipt of the correlation (40), determines one or more configuration parameters to be used for altering audio signals. In some embodiments, the determination of the configuration parameters includes setting an acoustic level of the input audio signal that caused the distraction of the user to be a distraction acoustic level threshold. In some embodiments the distraction acoustic level threshold is indicative of a volume of the input audio signal that caused the distraction of the user. When several input audio signal (i.e., several sounds) have caused the distraction, the acoustic level threshold may correspond to the minimum volume of the various input audio signals that caused the distraction.

In some embodiments, causing an alteration of the one or more audio signals includes causing any input audio signal that is received at the audio system 100, following the determination of the distraction, and which has an acoustic level that is greater or equal than the distraction acoustic level threshold to be blocked. In particular, the audio signal that caused the distraction is caused to be blocked from being output to the user. Alternatively, any ambient sound that has an acoustic level that is smaller than the distraction acoustic level threshold is still output to the user resulting in the user hearing only sounds that do not cause a distraction while avoiding to block all the sounds. In order to block the audio signal, the configuration parameters (e.g., the distraction acoustic level threshold) is used to configure the selective acoustic filtering unit 130 and/or the audio output 140 for blocking the audio signals output to the user. In these embodiments, the output audio signal(s) include signals that have been modified from the original input audio signals received at the audio system 100, where for example, some signals are output without modifications (signals with acoustic levels lower than the distraction threshold) and signals being blocked (signals with acoustic levels greater or equal than the distraction threshold).

In some embodiments, determining the configuration parameters may include, additionally or alternatively to determining the distraction acoustic level threshold, determining an acoustic level decrease parameter. In these embodiments, causing an alteration of the one or more audio signals includes causing an acoustic level of the audio signal that caused the distraction to be decreased based upon the acoustic level decrease parameter and the distraction acoustic level threshold, prior to being output to the user. In some embodiments, any input signal that has an acoustic level that is greater or equal to the distraction acoustic level threshold is caused to be modified based upon the acoustic level decrease parameter. For example, the volume of any of these sounds is lowered such that the distraction to the user is addressed (e.g., the lowered volume of the sounds no longer causes a distraction to the user or the level of distraction is reduced).

In order to decrease the acoustic level of the audio signal the configuration parameters (e.g., the distraction acoustic level threshold and the decrease parameter) are used to configure the selective acoustic filtering unit 130 and/or the audio output 140 for decreasing the volume of audio signals output to the user that have an acoustic level greater than the distraction acoustic level threshold. In these embodiments, the output audio signal(s) include signals that have been modified from the original input audio signals received at the audio system 100, where for example, some signals are output without modifications (signals with acoustic levels lower than the distraction threshold) and signals being lowered/decreased (signals with acoustic levels greater or equal than the distraction threshold).

In some embodiments, determining the configuration parameters may include, additionally or alternatively to determining the distraction acoustic level threshold, determining an acoustic level increase parameter. In these embodiments, causing an alteration of the one or more audio signals includes causing an acoustic level of an audio signal other than the one that caused the distraction to be increased based upon the acoustic level increase parameter, prior to being output to the user. For example, the PDU 125 may select the second input audio signal (6) to be increased to compensate for the distraction caused by audio signals received from the audio input 110. In other embodiments, the PDU 125 may determine to slightly increase other input audio signals (received from the audio input 110) and which have an acoustic level lower than the distraction acoustic level threshold.

In order to increase the acoustic level of the audio signal the configuration parameters (e.g., the distraction acoustic level threshold and the decrease parameter) are used to configure the selective acoustic filtering unit 130 and/or the audio output 140 for increasing the volume of audio signals output to the user (e.g., in some embodiments, increasing the volume of audio inputs that have an acoustic level smaller than the distraction acoustic level threshold). In these embodiments, the output audio signal(s) include signals that have been modified from the original input audio signals received at the audio system 100, where for example, some signals are output without modifications and signals being increased.

In some embodiments, several combinations of alteration can be performed without departing from the scope of the current invention. For example, an increase of certain sounds can be performed while simultaneously decreasing the volume of other sounds with the objective that the resulting modified audio signals output to the user address the distraction caused to the user (e.g., the output signals do not cause any distraction or alternatively cause a reduced distraction).

The embodiments described herein present clear advantages with respect to prior augmented hearing solutions. In contrast to the prior art solutions which do not take into consideration that surrounding and ambient sounds can cause distractions to the user, nor do they take into consideration the fact that a user may or may not hear an audio signal, the embodiments herein enable enhanced augmented hearing solutions that provide an adaptive alteration of input audio signals based upon the actual mental state of the user (e.g., whether the user is distracted and whether the user actually hears the sounds). The use of the correlation between the input audio signals, the AEP events, and the distraction events ensures that the system is reactive and adaptable based upon sounds that are heard and which actually cause a distraction to the user. In addition, in contrast to prior art solutions which completely block or cancel ambient sounds from being heard by a user, some embodiments herein enable a selective configuration of the audio output such that the user is still able to hear some sounds (either sounds that do not cause the distraction, or modified sounds (that caused the distraction or not)) but remain within an acceptable acoustic level which does not cause a distraction to the user.

Therefore, the embodiments of the present invention enable an active measuring of what the user is hearing and determining which acoustic sound level or which parts/elements of the sound cause a distraction to the user. The audio system 100 is operative to automatically respond with appropriate sound blocking and altering that are adapted to the changes that occur around the user and according to the user's preference. The invention further prevents situations that are created by standard audio-augmentation devices that can be perceived as unnatural (e.g., silences, distinctive audio filters, disconnect between sound and environment), by reducing the acoustic levels of sounds to a level that they are not distracting anymore (or where the distraction is reduced) such that these modified sounds are blended into the background noise.

The operations in the flow diagrams of FIGS. 5-8 will be described with reference to the exemplary embodiments of the other figures (FIGS. 1-4, 9-10B). However, it should be understood that the operations of the flow diagrams of FIGS. 5-8 can be performed by embodiments of the invention other than those discussed with reference to the other figures, and the embodiments of the invention discussed with reference to these other figures can perform operations different than those discussed with reference to the flow diagrams. While the flow diagrams in the figures show a particular order of operations performed by certain embodiments of the invention, it should be understood that such order is exemplary (e.g., alternative embodiments may perform the operations in a different order, combine certain operations, overlap certain operations, etc.).

Figure 5:
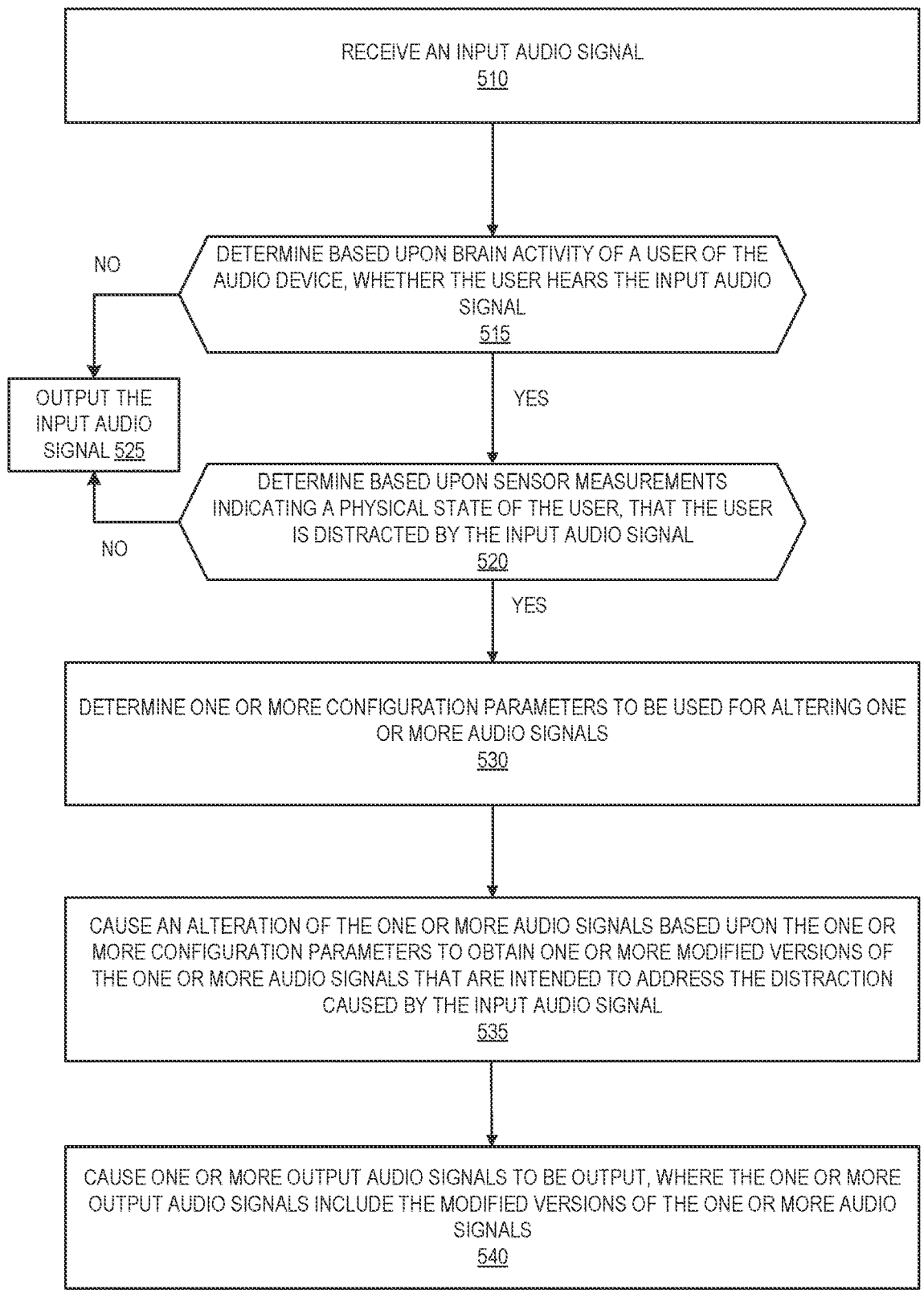
FIG. 5 illustrates a flow diagram of exemplary operations for enabling adaptive audio signal alteration in accordance with some embodiments.

FIG. 5 illustrates a flow diagram of exemplary operations for enabling adaptive audio signal alteration in accordance with some embodiments.

At operation 510, an audio signal is received. For example, the audio signal can be received as a first input audio signal in the audio input 110 of the audio system 100. Flow then moves to operation 515, at which a determination of whether the user hears the audio signal is performed, based upon brain activity of a user of the audio device. For example, the determination is performed at the ADU 115 based upon the sensor measurements (8a) and a correlation between the input audio signal and the AEP event is determined (3a). When it is determined that the user does not hear the audio signal flow then moves to operation 525 at which the audio signal is output.

Alternatively, when it is determined that the user hears the audio signal, the flow then moves to operation 520, at which a determination of whether the user is distracted by the audio signal is performed based upon sensor measurements indicating a physical state of the user. For example, the determination is performed at the DDU 120 of FIG. 1 based upon the sensor measurements (8b) and a correlation between the input audio signal and distraction events is output (4). When it is determined that the user is not distracted by the input audio signal, flow then moves to operation 525 at which the input audio signal is output.

In response to determining that the user hears the audio signal and that the audio signal causes the user to be distracted, the flow of operations moves to operation 530, at which a determination of one or more configuration parameters to be used for altering one or more audio signals, is performed. For example, the determination of the configuration parameters is performed by the PDU 125 upon receipt of the correlation between the AEP events and the input audio signal, and the correlation between the input audio signal and the distraction events.

Flow then moves to operation 535, at which an alteration of the one or more audio signals is performed based upon the one or more configuration parameters to obtain one or more modified versions of the one or more audio signals that are intended to address the distraction caused by the audio signal. In some embodiments, the configuration parameters are used to configure the audio output 140 that is operative to alter the audio signal prior to their output. In some additional or alternative embodiments, the configuration parameters are used to configure the sound adjustment unit 135 to alter the audio signal prior to their output. Flow then moves to operation 540, where the output audio signals are caused to be output. The output audio signals include the modified versions of the audio signals.

FIG. 6 illustrates a flow diagram of exemplary operations for determining, based upon brain activity of a user, whether a user of an audio device hears an audio signal, in accordance with some embodiments. For example, the operations can be performed by an ADU 115 of the audio system 100. At operation 610, electroencephalography (EEG) sensor measurements are received from an EEG sensor in an ear of the user. At operation 615 a correlation between the EEG sensor measurements and the input audio signal is determined. At operation 620 the correlation between the EEG sensor measurements and the audio signal is compared with auditory evoked potential (AEP) signatures (e.g., from the AEP signatures database) to determine whether the user hears the audio signal and to identify one or more AEP events associated with the audio signal. The AEP signatures are representative of EEG sensor measurements associated with audio signals. The ADU 115 outputs the correlation between the AEP events and the input audio signal indicating whether the user hears the input audio signal.

FIG. 7 illustrates a flow diagram of exemplary operations for determining, based upon sensor measurements indicating a physical state of the user, whether the user is distracted by an audio signal, in accordance with some embodiments. For example, the operations of the flow diagram of FIG. 7 are performed by the DDU 120. At operation 710, the DDU 120 determines that at least one of the sensor measurements indicates a physical state of the user is above a distraction threshold. Flow then moves to operation 715, at which a correlation between the at least one sensor measurement and the input audio signal is determined (e.g., correlation 4, between the first input audio signal and the distraction events).

Figure 8:
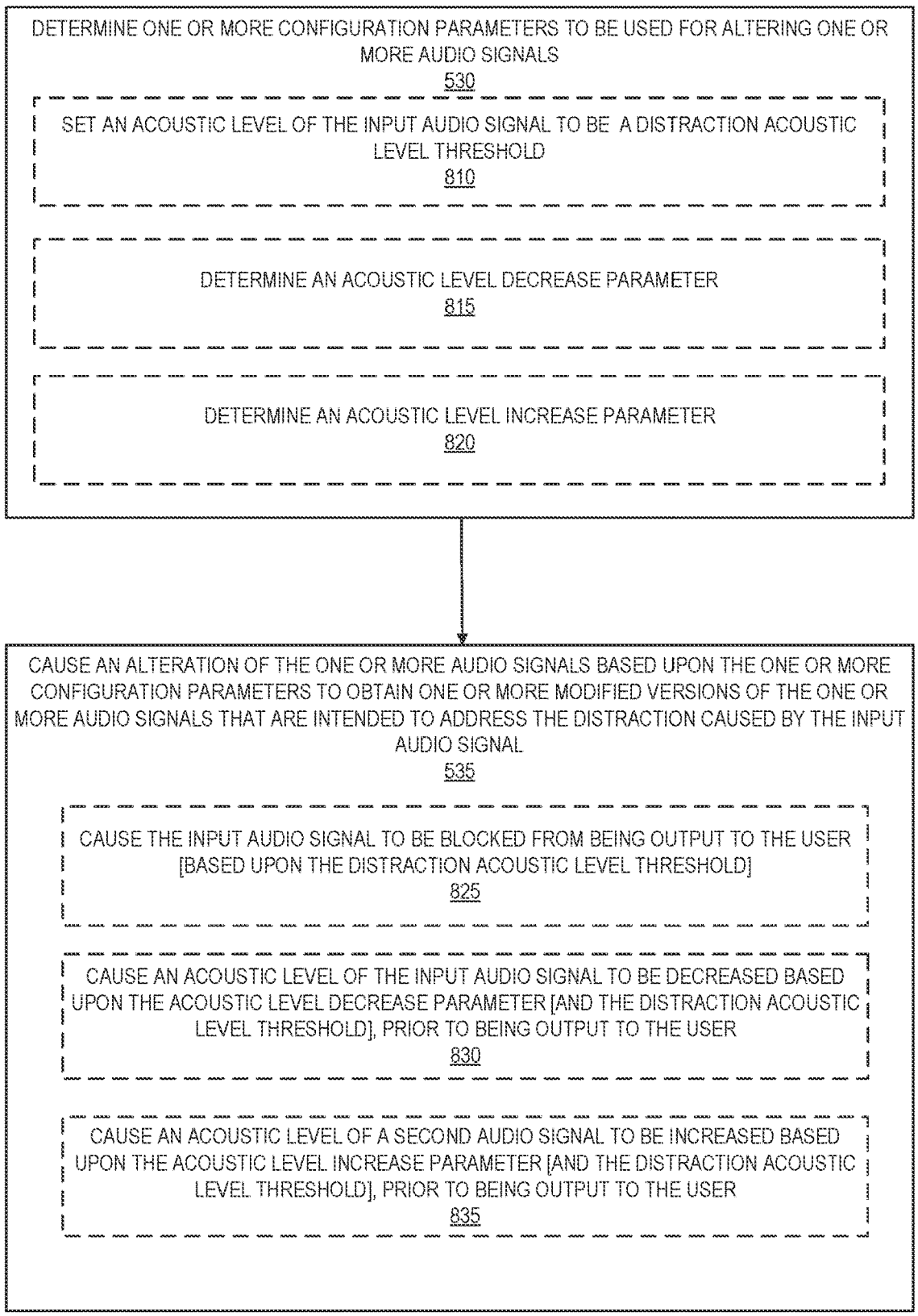
FIG. 8 illustrates a flow diagram of exemplary operations for alteration of audio signals, in accordance with some embodiments.

FIG. 8 illustrates a flow diagram of exemplary operations for alteration of audio signals, in accordance with some embodiments. Determining one or more configuration parameters to be used for altering one or more audio signals, at operation 530, may include setting an acoustic level of the input audio signal to be distraction acoustic level threshold (operation 810), determining an acoustic level decrease parameter (operation 815), and/or determining an acoustic level increase parameter (operation 820).

Causing, at operation 535, an alteration of the one or more audio signals based upon the one or more configuration parameters to obtain one or more modified versions of the one or more audio signals that are intended to address the distraction caused by the input audio signal may include: causing the input audio signal to be blocked from being output to the user based upon the distraction acoustic level threshold; causing an acoustic level of the input audio signal to be decreased based upon the acoustic level decrease parameter (and optionally the distraction acoustic level threshold), prior to being output to the user; and/or causing an acoustic level of a second audio signal to be increased based upon the acoustic level increase parameter (and optionally the distraction acoustic level threshold), prior to being output to the user.

In some embodiments, causing an alteration of the one or more audio signals includes causing any input audio signal that is received at the audio system 100, following the determination of the distraction, and which has an acoustic level that is greater or equal than the distraction acoustic level threshold to be blocked. In particular, the audio signal that caused the distraction is caused to be blocked from being output to the user. Alternatively, any ambient sound that has an acoustic level that is smaller than the distraction acoustic level threshold is still output to the user resulting in the user hearing only sounds that do not cause a distraction while avoiding to block all the sounds. In order to block the audio signal, the configuration parameters (e.g., the distraction acoustic level threshold) is used to configure the selective acoustic filtering unit 130 and/or the audio output 140 for blocking the audio signals output to the user. In these embodiments, the output audio signal(s) include signals that have been modified from the original input audio signals received at the audio system 100, where for example, some signals are output without modifications (signals with acoustic levels lower than the distraction threshold) and signals being blocked (signals with acoustic levels greater or equal than the distraction threshold).

In some embodiments, determining the configuration parameters may include, additionally or alternatively to determining the distraction acoustic level threshold, determining an acoustic level decrease parameter. In these embodiments, causing an alteration of the one or more audio signals includes causing an acoustic level of the audio signal that caused the distraction to be decreased based upon the acoustic level decrease parameter and the distraction acoustic level threshold, prior to being output to the user. In some embodiments, any input signal that has an acoustic level that is greater or equal to the distraction acoustic level threshold is caused to be modified based upon the acoustic level decrease parameter. For example, the volume of any of these sounds is lowered such that they are no longer causing a distraction to the user.

In order to decrease the acoustic level of the audio signal the configuration parameters (e.g., the distraction acoustic level threshold and the decrease parameter) are used to configure the selective acoustic filtering unit 130 and/or the audio output 140 for decreasing the volume of audio signals output to the user that have an acoustic level greater than the distraction acoustic level threshold. In these embodiments, the output audio signal(s) include signals that have been modified from the original input audio signals received at the audio system 100, where for example, some signals are output without modifications (signals with acoustic levels lower than the distraction threshold) and signals being lowered/decreased (signals with acoustic levels greater or equal than the distraction threshold).

In some embodiments, determining the configuration parameters may include, additionally or alternatively to determining the distraction acoustic level threshold, determining an acoustic level increase parameter. In these embodiments, causing an alteration of the one or more audio signals includes causing an acoustic level of an audio signal other than the one that caused the distraction to be increased based upon the acoustic level increase parameter, prior to being output to the user. For example, the PDU 125 may select the second input audio signal (6) to be increased to compensate for the distraction caused by audio signals received from the audio input 110. In other embodiments, the PDU 125 may determine to slightly increase other input audio signals (received from the audio input 110) and which have an acoustic level lower than the distraction acoustic level threshold.

In order to increase the acoustic level of the audio signal the configuration parameters (e.g., the distraction acoustic level threshold and the decrease parameter) are used to configure the selective acoustic filtering unit 130 and/or the audio output 140 for increasing the volume of audio signals output to the user (e.g., in some embodiments, increasing the volume of audio inputs that have an acoustic level smaller than the distraction acoustic level threshold). In these embodiments, the output audio signal(s) include signals that have been modified from the original input audio signals received at the audio system 100, where for example, some signals are output without modifications and signals being increased.

In an alternative embodiment, the alteration of the input audio signal can be performed to enable an improved detection of the user's ASSR. For example, upon detection of a distraction caused by an input audio signal, the audio output 140 and the selective acoustic filtering unit 130 are configured to modulate characteristics (e.g., the amplitude) of the input audio signal with a pre-determined frequency. The EEG sensor measurement are then analyzed by the ADU 115 and the DDU 120 to determine if there is a measurable correlation with the modified audio signal (when modified based upon the pre-determined frequency). This process can be repeated multiple times in order to select a distraction acoustic level threshold that probes the ASSR without causing a distraction.

In some embodiments, several combinations of alterations can be performed without departing from the scope of the current invention. For example, an increase of the volume of certain sounds can be performed while simultaneously decreasing the volume of other sounds with the objective that the resulting modified audio signals output to the user do not cause any distraction.

While the embodiments of the invention have been described in relation to the first input audio signal(s) received at the audio input 110 being analyzed, in other embodiments, can be contemplated where the audio signal(s) being analyzed are the output audio signals(s) output at the audio output 140. Such embodiments can be implemented such that each of the components of the audio signal adaptive alteration unit 160 (ADU 115, DDU 120 and the PDU 125) may receive the output audio signal(s) to analyze instead of or in addition to the first input audio signal(s). The output audio signal(s) may include modified version of the first input audio signal(S) that have been modified (e.g., the sound has been changed, etc.) and which can still cause a distraction to the user. The modified audio signals can be a result of a first pass of adaptive audio signal alteration performed by the audio signal adaptive alteration unit 160 on the original ambient sounds (i.e., the first input audio signals). Thus, similarly to the previous embodiments, where the first input audio signal representing ambient sounds in the environment of the user are being monitored and adaptively altered to not cause a distraction of the user, the alternative embodiments ensure that these altered sounds (i.e., the modified audio signal) are also monitored and altered if necessary such that they do not cause a distraction of the user.

In an alternative embodiment, the audio system 100 is operative to substantially block all the first input audio signals received at the audio input 110 and gradually alter the input audio signal to obtain modified audio signals that are output to the user. These gradually modified audio signals may be modified such that their volume is gradually increased over a period of time and a detection is performed when a given volume causes a distraction of the user. The acoustic level of the modified audio signal causing the distraction can then be used as a distraction acoustic level threshold for altering and modifying future incoming audio inputs that are output to the user. Consequently, the system 100 adapts the input audio signals to a level that is comfortable to the user and which does not cause any distraction without causing a complete and total cancellation of the ambient audio signals/sounds.

The various embodiments described herein present clear advantages with respect to prior augmented hearing solutions. In contrast to the prior art solutions which do not take into consideration that surrounding and ambient sounds can cause distractions to the user, nor do they take into consideration the fact that a user may or may not hear an audio signal, the embodiments herein enable enhanced augmented hearing solution that provide an adaptive alteration of input audio signals based upon the actual state of the user (e.g., whether the user is distracted and whether the user actually hears the sounds). The use of the correlation between the input audio signals, the AEP events, and the distraction events ensures that the system is reactive and adaptable based upon sounds that are heard and which actually cause a distraction to the user. In addition, in contrast to prior art solutions which completely block or cancel ambient sounds from being heard by a user, some embodiments herein enable a selective configuration of the audio output such that the user is still able to hear some sounds (either sounds that did not cause the distraction, or modified sounds (that caused the distraction or not)) but remain within an acceptable acoustic level which does not cause a distraction to the user.

The embodiments of the present invention enable an active measuring of what the user is hearing and determining which acoustic sound level or which parts/elements of the sound cause a distraction to the user. The audio system 100 is operative to automatically respond with appropriate sound blocking and altering that are adapted to the changes that occur around the user and according to the user's preference. The invention further prevents situations that are created by audio-augmentation devices that can be perceived as unnatural (e.g. silences, distinctive audio filters, disconnect between sound and environment), by reducing the acoustic levels of sounds to a level that they are not distracting anymore but instead where they are blended into the background noise.

Architecture:

An electronic device stores and transmits (internally and/or with other electronic devices over a network) code (which is composed of software instructions and which is sometimes referred to as computer program code or a computer program) and/or data using machine-readable media (also called computer-readable media), such as machine-readable storage media (e.g., magnetic disks, optical disks, solid state drives, read only memory (ROM), flash memory devices, phase change memory) and machine-readable transmission media (also called a carrier) (e.g., electrical, optical, radio, acoustical or other form of propagated signals—such as carrier waves, infrared signals). Thus, an electronic device (e.g., a computer) includes hardware and software, such as a set of one or more processors (e.g., wherein a processor is a microprocessor, controller, microcontroller, central processing unit, digital signal processor, application specific integrated circuit, field programmable gate array, other electronic circuitry, a combination of one or more of the preceding) coupled to one or more machine-readable storage media to store code for execution on the set of processors and/or to store data. For instance, an electronic device may include non-volatile memory containing the code since the non-volatile memory can persist code/data even when the electronic device is turned off (when power is removed), and while the electronic device is turned on that part of the code that is to be executed by the processor(s) of that electronic device is typically copied from the slower non-volatile memory into volatile memory (e.g., dynamic random access memory (DRAM), static random access memory (SRAM)) of that electronic device.

Figure 9:
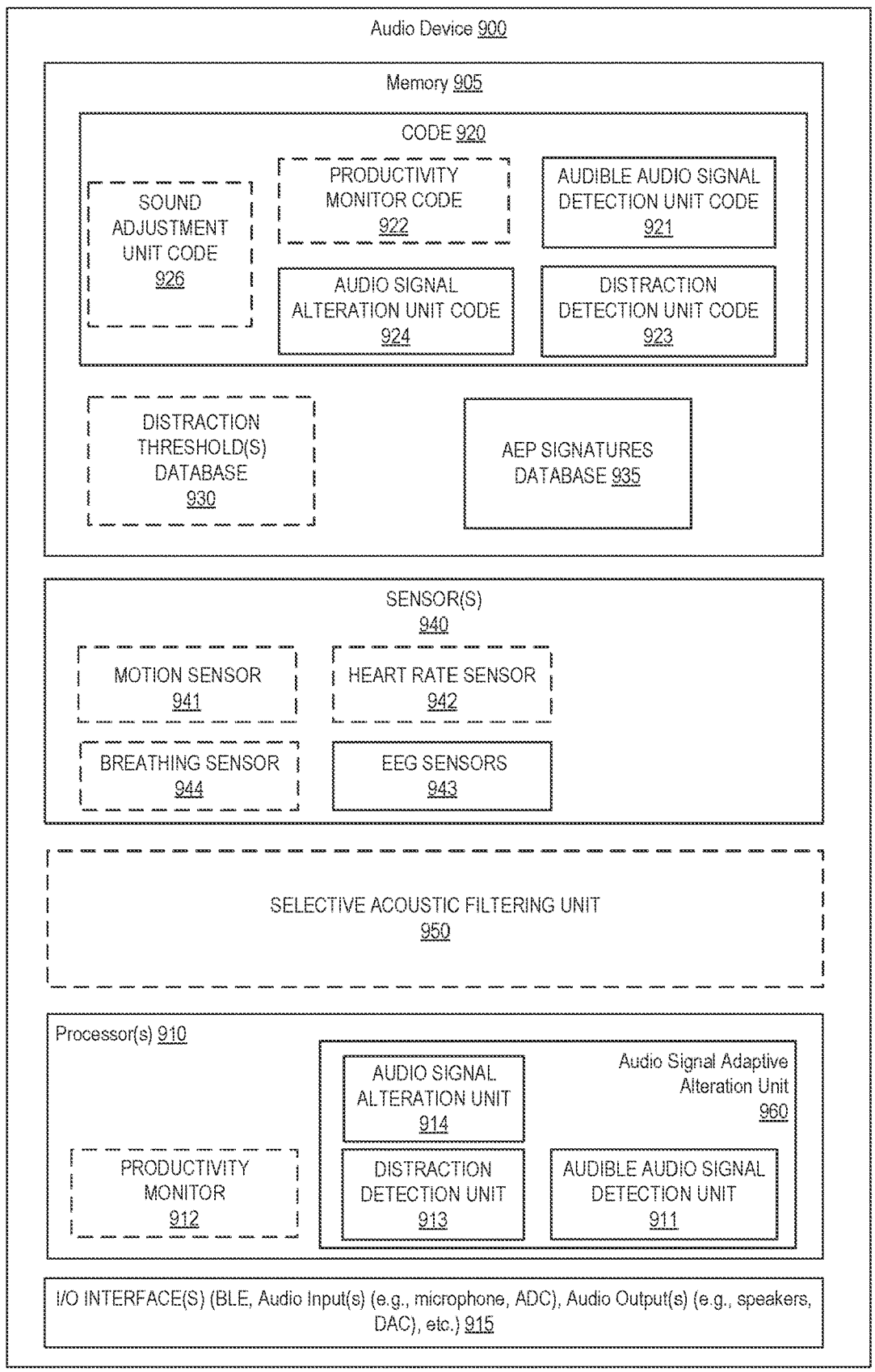
FIG. 9 illustrates a block diagram of an exemplary implementation of audio system for enabling adaptive audio signal alteration, in accordance with some embodiments.

The audio system 100 can be implemented on one or more electronic devices as will be described with reference to the following figures. FIG. 9 illustrates a block diagram of an exemplary implementation of an audio system for enabling adaptive audio signal alteration, in accordance with one embodiment. The physical (i.e., hardware) audio device 900 is an electronic device that can perform some or all of the operations and methods described above for one or more of the embodiments. The physical audio device 900 can include one or more I/O interfaces, processor(s) ("processor circuitry") 910, memory 905, one or more sensors(s) 940, and an optional selective acoustic filtering unit 950.

The processor(s) 910 may include one or more data processing circuits, such as a general purpose and/or special purpose processor (e.g., microprocessor and/or digital signal processor). The processor(s) is configured to execute the audio signal adaptive alteration unit 160 (that include the audio signal alteration unit 914, the distraction detection unit 913, and the audible audio signal detection unit 911), and optionally configured to execute the productivity monitor 912. In some embodiments, the productivity monitor is executed on another electronic device external to the audio device 900. The audio signal adaptive unit 960 when executed by the processor is operative to perform the operations described with reference to the FIGS. 1-8. For example, the audio signal alteration unit 914, the distraction detection unit 913, and the audible audio signal detection unit 911 when executed by the processor are operative to perform the operations described with reference to the PDU 125, the DDU 120, and the ADU 115 respectively. Although the various modules of FIG. 9 are shown to be included as part of the processor 910, one having ordinary skill in the art will appreciate that the various modules may be stored separately from the processor, for example, in a non-transitory computer readable storage medium. The processor can execute the various modules stored in the memory (e.g., productivity monitor code 922, the audible audio signal detection unit code 921, the distraction detection unit code 923, the audio signal alteration unit code 924, and the sound adjustment unit code 926), to perform some or all of the operations and methods described above. Accordingly, the processor can be configured by execution of various modules to carry out some or all of the functionality disclosed herein. The audio device 900 further includes an AEP signature database 935 and an optional distraction threshold database 930, stored in the memory 905.

The audio device 900 includes the sensor(s) 940. The sensors 940 includes EEG sensors (which can be in-ear EEG sensors) as well as a set of one or more sensors that are operative to determine a physical state of the user. In some embodiments, the sensor(s) 940 can include one or several of the following sensor(s): a motion sensor 941, a heart rate sensor 31, a breathing sensor 944, and a hear rate sensor 942.

The audio device 900 also includes a set of one or more physical Input/Output (I/O) interface(s) to establish connections and communication between the different components of the audio device 900 and with external electronic devices. For example, the set of I/O interfaces can include a microphone and an ADC for receiving input audio signals, speakers, and a DAC for outputting audio signals to a user, a secondary audio input for receiving other audio signals, and a communication interface (e.g., BLE) for communicating with external electronic devices.

Figure 10A:
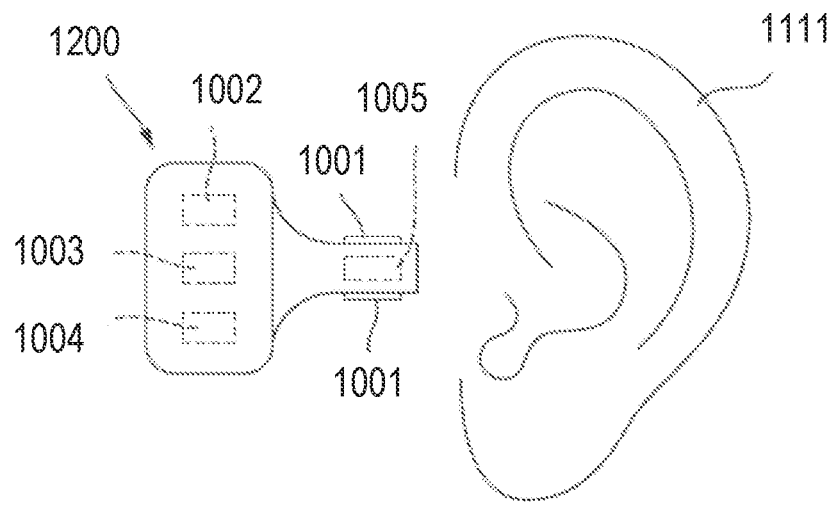
FIGS. 10A-B illustrate exemplary implementations of the audio system for enabling adaptive audio signal alteration, in accordance with some embodiments.
Figure 10B:
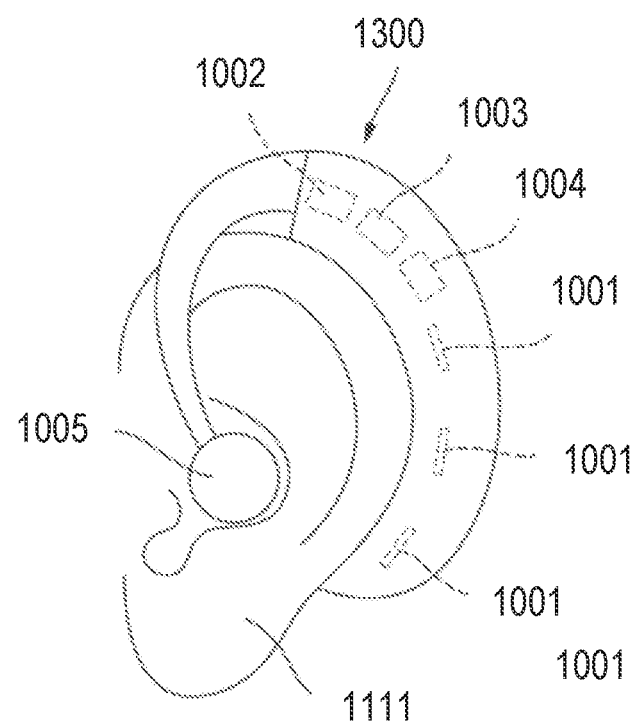

FIG. 10A-B illustrate exemplary implementations of the audio system for enabling adaptive audio signal alteration, in accordance with some embodiments. With reference to FIG. 10A, the electronic device 1200 is an exemplary implementation of the audio device 900, where all the elements of this device are included within a single apparatus according to a first exemplary design that is arranged for contacting a skin of the user inside the ear channel of the ear 1111. The audio device 1200 includes processing unit 1003 (which includes one or more processors and a memory) and an I/O interface 1004, EEG sensors 1101 arranged for contacting a skin of a user inside the ear channel of ear 1111, and at least one motion sensor 1002 for measuring a movement of the head. Similar to what is described with reference to audio device 900 hereinbefore, electronic device 1200 is operative to perform the operations described with reference to the FIGS. 1-8.

With reference to FIG. 10B, yet a further embodiment 1300 of the audio device 900 for enabling adaptive audio signal alteration is described, where all the elements of this device are included within a single apparatus according to a second exemplary design that is arranged for contacting a skin of the user inside the ear channel of the ear 1111. The audio device 1300 includes processing unit 1003 (which includes one or more processors and a memory) and an I/O interface 1004, EEG sensors 1001 arranged for contacting a skin of a user inside the ear channel of ear 1111, and at least one motion sensor 1002 for measuring a movement of the head. Similar to what is described with reference to audio device 900 hereinbefore, electronic device 1300 is operative to perform the operations described with reference to the FIGS. 1-8.

While the invention has been described in terms of an audio system 100 being implemented within a single physical electronic device (e.g., audio device 900, audio device 1200 and audio device 1300), those skilled in the art will recognize that the invention is not limited to these embodiments. For example, other embodiments can be contemplated where parts of the audio system 100 are included in separate audio devices. In one exemplary embodiments, the sensors(s) 150, the audio input 110, the audio output 140, the optional selective acoustic filtering unit 130 and the I/O unit 145 can be included in a first electronic device to be worn on the user and that is communicatively coupled (e.g., through BLE interfaces) with a second electronic device (e.g., a smartphone, a computer, or any other type of electronic device) including the audio signal adaptive alteration unit 160. Other combinations and embodiments can be implemented without departing from the scope of the present invention.

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A method of enabling adaptive audio signal alteration, the method comprising:
  receiving one or more audio signals including an input audio signal for a user;

in response to receiving the input audio signal, receiving electroencephalography (EEG) sensor measurements representative of brain activity of the user;

determining, based upon the input audio signal and the EEG sensor measurements, a correlation that indicates whether the user hears the input audio signal;

in response to the correlation indicating that the user hears the input signal, determining, based upon sensor measurements indicating a state of the user, whether the input audio signal causes the user to be distracted; and in response to determining that the input audio signal causes the user to be distracted, causing an alteration of one of the one or more audio signals to obtain a modified version of the one of the one or more audio signals to address a distraction caused by the input audio signal when heard by the user.

2. The method of claim 1, wherein in response to determining that the user hears the input audio signal and that the input audio signal causes the user to be distracted, further causing one or more output audio signals including the modified version of the one of the one or more audio signals to be output.

3. The method of claim 1, wherein the determining the correlation that indicates whether the user hears the input audio signal further includes:

comparing the EEG sensor measurements and the input audio signal with Auditory Evoked Potential (AEP) signatures for the correlation.

4. The method of claim 1, in response to determining that the user hears the input audio signal and that the input audio signal causes the user to be distracted, further determining one or more configuration parameters to be used for altering one of the one or more audio signals.

5. The method of claim 4, wherein the determining the one or more configuration parameters to be used for altering the one of the one or more audio signals includes setting an acoustic level of the input audio signal to be a distraction acoustic level threshold.

6. The method of claim 1, wherein the sensor measurements include at least one of EEG sensor measurements, motion sensor measurements, heart rate sensor measurements, breathing sensor measurements, and productivity monitoring indicators.

7. An apparatus for enabling adaptive audio signal alteration, the apparatus comprising:

a processor configured to execute instructions stored in a non-transitory computer readable storage medium to perform operations to:

receive one or more audio signals including an input audio signal for a user;

in response to receiving the input audio signal, receive electroencephalography (EEG) sensor measurements representative of brain activity of the user;

determine, based upon the input audio signal and the EEG sensor measurements, a correlation that indicates whether the user hears the input audio signal;

in response to the correlation indicating that the user hears the input signal, determine, based upon sensor measurements indicating a state of the user, whether the input audio signal causes the user to be distracted; and in response to determining that the input audio signal causes the user to be distracted, cause an alteration of one of the one or more audio signals to obtain a modified version of the one of the one or more audio signals to address a distraction caused by the input audio signal when heard by the user.

8. The apparatus of claim 7, wherein in response to determining that the user hears the input audio signal and that the input audio signal causes the user to be distracted, further causing one or more output audio signals including the modified version of the one of the one or more audio signals to be output.

9. The apparatus of claim 7, wherein determining the correlation that indicates whether the user hears the input audio signal further includes:

comparing the EEG sensor measurements and the input audio signal with Auditory Evoked Potential (AEP) signatures for the correlation.

10. The apparatus of claim 7, in response to determining that the user hears the input audio signal and that the input audio signal causes the user to be distracted, further to perform operations to determine one or more configuration parameters to be used for altering one of the one or more audio signals.

11. The apparatus of claim 10, wherein determining the one or more configuration parameters to be used for altering the one of the one or more audio signals includes operations to set an acoustic level of the input audio signal to be a distraction acoustic level threshold.

12. The apparatus of claim 7, wherein the sensor measurements include at least one of EEG sensor measurements, motion sensor measurements, heart rate sensor measurements, breathing sensor measurements, and productivity monitoring indicators.

13. A non-transitory computer readable storage medium that stores instructions, which when executed by a processor perform operations comprising:

receiving one or more audio signals including an input audio signal for a user;

in response to receiving the input audio signal, receiving electroencephalography (EEG) sensor measurements representative of brain activity of the user;

determining, based upon the input audio signal and the EEG sensor measurements, a correlation that indicates whether the user hears the input audio signal;

in response to the correlation indicating that the user hears the input signal, determining, based upon sensor measurements indicating a state of the user, whether the input audio signal causes the user to be distracted; and in response to determining that the input audio signal causes the user to be distracted, causing an alteration of one of the one or more audio signals to obtain a modified version of the one of the one or more audio signals to address a distraction caused by the input audio signal when heard by the user.

14. The non-transitory computer readable storage medium of claim 13, wherein in response to determining that the user hears the input audio signal and that the input audio signal causes the user to be distracted, further causing one or more output audio signals including the modified version of the one of the one or more audio signals to be output.

15. The non-transitory computer readable storage medium of claim 13, wherein the determining the correlation that indicates whether the user hears the input audio signal further includes:

comparing the EEG sensor measurements and the input audio signal with Auditory Evoked Potential (AEP) signatures for the correlation.

16. The non-transitory computer readable storage medium of claim 13, in response to determining that the user hears the input audio signal and that the input audio signal causes the user to be distracted, further determining one or more configuration parameters to be used for altering one of the one or more audio signals.

17. The non-transitory computer readable storage medium of claim 16, wherein the determining the one or more configuration parameters to be used for altering the one of the one or more audio signals includes setting an acoustic level of the input audio signal to be a distraction acoustic level threshold.

18. The non-transitory computer readable storage medium of claim 13, wherein the sensor measurements include at least one of EEG sensor measurements, motion sensor measurements, heart rate sensor measurements, breathing sensor measurements, and productivity monitoring indicators.

* * * * *